US012310887B1

(12) United States Patent
Fix

(10) Patent No.: US 12,310,887 B1
(45) Date of Patent: May 27, 2025

(54) LIGHT PATTERNS FOR CORNEAL TOPOGRAPHY

(71) Applicant: Meta Platforms Technologies, LLC, Menlo Park, CA (US)

(72) Inventor: Alexander Jobe Fix, Seattle, WA (US)

(73) Assignee: Meta Platforms Technologies, LLC, Menlo Park, CA (US)

( * ) Notice: Subject to any disclaimer, the term of this patent is extended or adjusted under 35 U.S.C. 154(b) by 106 days.

(21) Appl. No.: 17/896,765

(22) Filed: Aug. 26, 2022

Related U.S. Application Data

(63) Continuation of application No. 16/692,547, filed on Nov. 22, 2019, now Pat. No. 11,458,040.

(Continued)

(51) Int. Cl.
*A61B 3/10* (2006.01)
*A61B 3/00* (2006.01)
(Continued)

(52) U.S. Cl.
CPC ............ *A61F 9/007* (2013.01); *A61B 3/0008* (2013.01); *A61B 3/0025* (2013.01); *A61B 3/107* (2013.01);
(Continued)

(58) Field of Classification Search
CPC ........... A61B 3/103; A61B 3/14; A61B 3/152; A61B 3/113; A61B 3/1225; A61B 3/024; A61B 3/032; A61B 3/18; A61B 3/1015; G02C 5/00; G09G 2340/0492; G02B 27/0093; G02B 27/0101; G02B 27/0172; G02B 27/01
(Continued)

(56) References Cited

U.S. PATENT DOCUMENTS 11,458,040 B2   10/2022 Fix
2005/0175218 A1   8/2005 Vertegaal et al.
(Continued)

OTHER PUBLICATIONS

"Badly Fragmented' Forensic Science System Needs Overhaul; Evidence to Support Reliability of Many Techniques is Lacking," National Academies of Sciences, Engineering, and Medicine [online], Retrieved on Jan. 3, 2019, 8 Pages, Retrieved from the Internet: URL: http://www8.nationalacademies.org/onpinews/newsitem.aspx?recordid=12589.

(Continued)

*Primary Examiner* — Dawayne Pinkney
(74) *Attorney, Agent, or Firm* — Greenberg Traurig, LLP

(57) ABSTRACT

Techniques are described for generating and using an illumination pattern for corneal topography. In some examples, the illumination pattern is projected over a sequence of frames, including a first frame with a first pattern of dots arranged along a two-dimensional grid, and a second frame with a second pattern of dots arranged along the two-dimensional grid. The first pattern differs from the second pattern with respect to a wavelength of light used to project one or more dots, a position of one or more dots, or both. After the illumination pattern has been determined, it can be projected over the sequence of frames and onto an eye of a user. Reflections of the illumination pattern as projected over the sequence of frames can then be used to calculate an eye model characterizing a topography of a cornea of the eye of the user.

20 Claims, 10 Drawing Sheets

Related U.S. Application Data

(60) Provisional application No. 62/796,031, filed on Jan. 23, 2019.

(51) Int. Cl.

| | | |
|---|---|---|
| *A61B 3/107* | (2006.01) | |
| *A61B 3/14* | (2006.01) | |
| *A61F 9/007* | (2006.01) | |
| *G02C 5/00* | (2006.01) | |
| *A61F 9/00* | (2006.01) | |
| *A61F 9/008* | (2006.01) | |

(52) U.S. Cl.
CPC ........ *A61B 3/14* (2013.01); *A61F 2009/0052* (2013.01); *A61F 2009/00872* (2013.01); *A61F 2009/00882* (2013.01)

(58) Field of Classification Search
USPC ................ 351/212, 200, 205–206, 208–211, 351/221–223, 245–245, 41; 345/649
See application file for complete search history.

(56) References Cited

U.S. PATENT DOCUMENTS

| | | |
|---|---|---|
| 2009/0316115 A1 | 12/2009 | Itoh et al. |
| 2014/0289323 A1 | 9/2014 | Kutaragi et al. |
| 2015/0131055 A1* | 5/2015 | Catanzariti .......... A61B 3/0091 351/212 |
| 2015/0193920 A1 | 7/2015 | Knee et al. |
| 2015/0326570 A1 | 11/2015 | Publicover et al. |
| 2017/0123526 A1 | 5/2017 | Trail et al. |
| 2017/0192499 A1* | 7/2017 | Trail ....................... G06F 1/163 |
| 2018/0193194 A1* | 7/2018 | Haeggström ........... A61F 9/008 |
| 2018/0235465 A1 | 8/2018 | Calpe Maravilla et al. |
| 2018/0239423 A1* | 8/2018 | Mardanbegi ........... G06F 3/013 |
| 2018/0329489 A1 | 11/2018 | Price et al. |
| 2018/0366045 A1 | 12/2018 | Perreault et al. |
| 2019/0042842 A1* | 2/2019 | Cavin ................. G06V 40/197 |
| 2019/0139088 A1 | 5/2019 | Brownhill et al. |

OTHER PUBLICATIONS

Bashkatov A.N., et al., "Optical Properties of Human Sclera in Spectral Range 370-2500 nm," Optics and Spectroscopy, 2010, vol. 109 (2), pp. 197-204.

Derakhshani R., et al., "A Texture-Based Neural Network Classifier for Biometric Identification using Ocular Surface Vasculature," Appeared in Proceedings of International Joint Conference on Neural Networks, Aug. 2007, 6 pages.

Final Office Action mailed Jun. 18, 2020 for U.S. Appl. No. 16/206,769, filed Nov. 30, 2018, 12 pages.

Final Office Action mailed Apr. 20, 2022 for U.S. Appl. No. 16/692,547, filed Nov. 22, 2019, 9 pages.

Green M.A., et al., "Optical Properties of Intrinsic Silicon at 300° K," Progress in Photovoltaics: Research and Application, 1995, vol. 3, pp. 189-192.

"Iris Recognition vs. Retina Scanning—What are the Differences?," M2SYS Blog on Biometrics Technology [online], Retrieved on Jan. 3, 2019, 6 Pages, Retrieved from the Internet: URL: http://www.m2sys.com/blog/biometric-hardware/iris-recognition-vs-retina-scanning-what-are-the-differences.

Non-Final Office Action mailed Oct. 21, 2021 for U.S. Appl. No. 16/692,547, filed Nov. 22, 2019, 7 pages.

Non-Final Office Action mailed Jan. 27, 2020 for U.S. Appl. No. 16/206,769, filed Nov. 30, 2018, 10 pages.

Notice of Allowance mailed May 26, 2022 for U.S. Appl. No. 16/692,547, filed Nov. 22, 2019, 8 pages.

Prahl S., "Optical Absorption of Hemoglobin," Retrieved on Jan. 3, 2019, 5 Pages, Retrieved from the Internet: URL: http://omlc.org/spectra/hemoglobin/.

* cited by examiner

LIGHT PATTERNS FOR CORNEAL TOPOGRAPHY

CROSS-REFERENCE TO RELATED APPLICATIONS

This application is a continuation of U.S. Non-Provisional application Ser. No. 16/692,547, filed Nov. 22, 2019, entitled "Corneal Topography Mapping With Dense Illumination" which claims the benefit of and priority to U.S. Provisional Application No. 62/796,031, filed Jan. 23, 2019, entitled "Corneal Topography Mapping With Dense Illumination." The content of U.S. Non-Provisional application Ser. No. 16/692,547 and U.S. Provisional Application No. 62/796, 031 are incorporated herein by reference in their entirety.

BACKGROUND

Corneal topography refers to the mapping of the surface of the cornea. Corneal topography has been used to diagnose and treat medical conditions of the eye and is performed in a clinical setting using a corneal topograph, which is a device that projects an illumination pattern of concentric rings, known as Placido rings, onto the eye. The topology of the cornea is then computed based on the reflected pattern. Corneal topographs are large and need to operated by a trained professional, and are therefore unsuitable for use in portable devices, such as head-mounted displays (HMDs).

HMDs are a wearable form of near-eye display (NED) and are sometimes used for displaying content in an augmented reality (AR) or virtual reality (VR) system. Various eye tracking schemes have been applied in HMDs and rely on placing a few light sources outside of the user's field of view. In a conventional eye tracking scheme, the cornea is assumed to be a perfect sphere.

BRIEF DESCRIPTION OF THE DRAWINGS

Illustrative embodiments are described with reference to the following figures.

Figure 1:
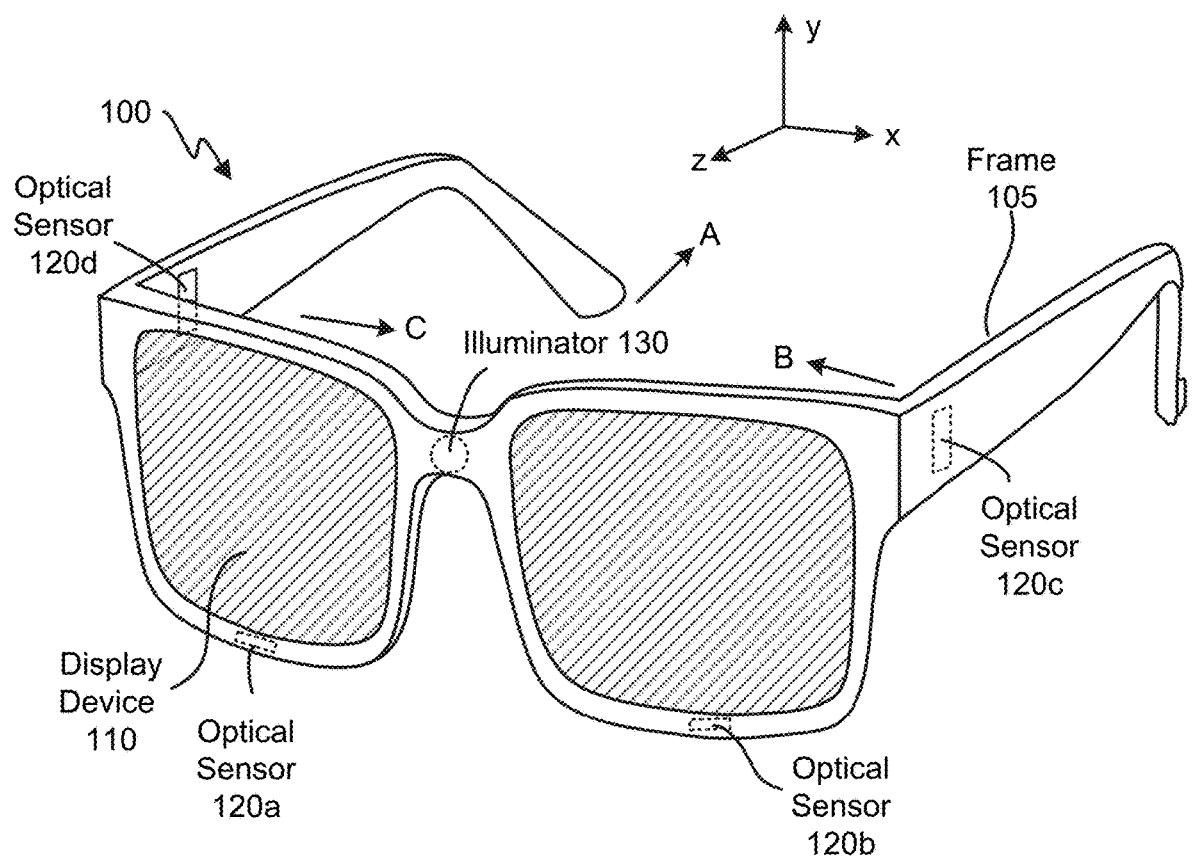
FIG. 1 shows a near-eye display, in accordance with an embodiment.
Figure 1:
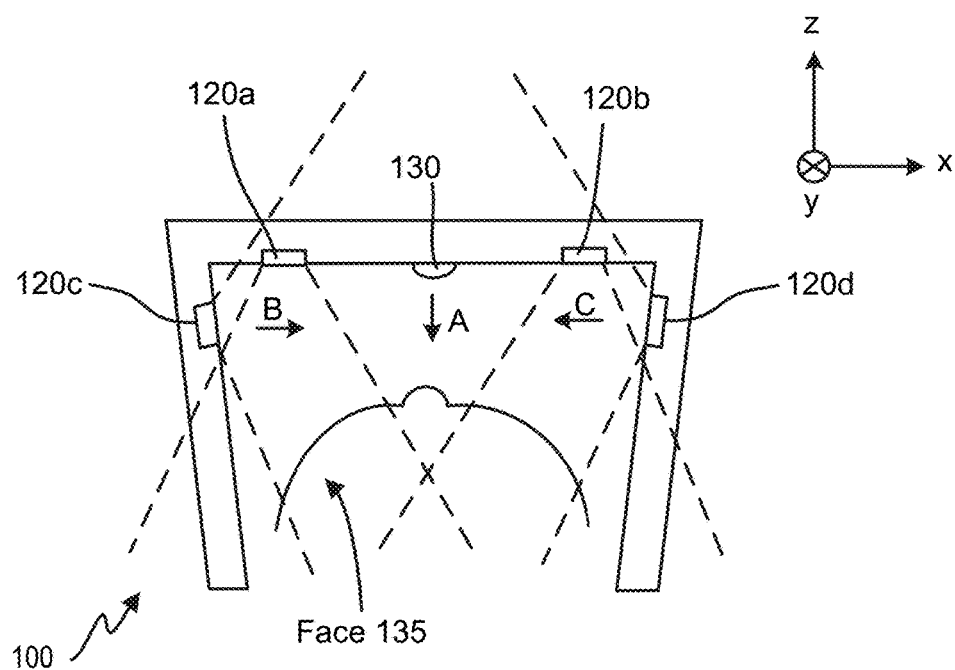

The figures depict embodiments of the present disclosure for purposes of illustration only. One skilled in the art will readily recognize from the following description that alternative embodiments of the structures and methods illustrated may be employed without departing from the principles, or benefits touted, of this disclosure.

In the appended figures, similar components and/or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

In the following description, for the purposes of explanation, specific details are set forth in order to provide a thorough understanding of certain inventive embodiments. However, it will be apparent that various embodiments may be practiced without these specific details. The figures and description are not intended to be restrictive.

Example embodiments relate to a system and methods for performing corneal topography in an HMD. In an example embodiment, the topography of the cornea is determined using reflections (also referred to herein as glints) produced by illuminating the surface of the eye with a dot pattern. The dot pattern can be generated using a dense array of illuminators (e.g., 100 or more points of illumination), which can be positioned within a field of view of the user, i.e., dense, in-field illumination. This is in contrast to eye tracking methods that may rely on only a few light sources positioned at the periphery of the user's field of view. In-field illumination may offer greater eye-tracking accuracy than positioning the light sources at the periphery of the user's field of view. For example, the probability of capturing glints over all gaze angles of the eye is higher when the light sources are located within the user's field of view.

Further, the use of dense illumination in the form of a dot pattern enables capturing of many reflections off the eye, providing a rich data set for use in reconstructing the shape of the cornea for use in eye tracking or other applications. The dot pattern can be projected without the use of a corneal topograph, and a corneal topography procedure can be automated so as not to require the supervision of a trained professional. In one embodiment, the number of illuminators is reduced (e.g., to a single point source) by generating the illumination pattern using holographic projection or other methods capable of producing an illumination pattern from a point source.

Example embodiments relate to the formation of an illumination pattern comprising an array of dots that are encoded so that the dots are individually identifiable in a reflected pattern. In one embodiment, the illumination pattern is generated as a non-rectilinear pattern shaped so that the illumination pattern becomes rectilinear or substantially rectilinear when reflected off the surface of the cornea. Making the reflected pattern rectilinear or substantially rectilinear facilitates comparison of the reflected pattern to a reference pattern, which may also be rectilinear.

Example embodiments relate to a system and methods for applying an eye model generated using corneal topography. In one embodiment, the eye model is used to perform eye tracking by comparing the eye model to data from subsequently captured images of the eye. In particular, movements of the eye can be determined using reflections off the cornea (glint only) or using glints in combination with tracking of other eye features such as the pupil or iris.

Embodiments of the present disclosure may include or be implemented in conjunction with an artificial reality system. Artificial reality is a form of reality that has been adjusted in some manner before presentation to a user, which may include, e.g., a VR, an AR, a mixed reality (MR), a hybrid reality, or some combination and/or derivatives thereof. Artificial reality content may include completely generated content or generated content combined with captured (e.g., real-world) content. The artificial reality content may include video, audio, haptic feedback, or some combination thereof, and any of which may be presented in a single channel or in multiple channels (such as stereo video that produces a three-dimensional effect to the viewer). Additionally, in some embodiments, artificial reality may also be associated with applications, products, accessories, services, or some combination thereof, that are used to, e.g., create content in an artificial reality and/or are otherwise used in (e.g., perform activities in) an artificial reality. The artificial reality system that provides the artificial reality content may be implemented on various platforms, including an NED connected to a host computer system, a standalone NED, a mobile device or computing system, or any other hardware platform capable of providing artificial reality content to one or more viewers.

FIG. 1 shows an NED 100 according to an embodiment of the present disclosure. The NED 100 presents media to a user. Examples of media presented by the NED 100 include one or more images, video, and/or audio. In some embodiments, audio is presented via an external device (e.g., speakers and/or headphones) that receives audio information from the NED 100, a console, or both, and presents audio output based on the audio information. The NED 100 can be configured to operate as a VR display. In some embodiments, the NED 100 is modified to operate as an AR display and/or an MR display.

The NED 100 includes a frame 105 and a display device 110. The frame 105 is shaped to enable the NED 100 to be worn in the manner of a pair of eyeglasses. Thus, the NED 100 is an example of an HMD. The frame 105 is coupled to one or more optical elements. The display device 110 is configured for the user to see content presented by NED 100. In some embodiments, the display device 110 comprises a waveguide display assembly for directing light from one or more images to an eye of the user.

The NED 100 further includes optical sensors 120a, 120b, 120c, and 120d. Each of the optical sensors 120a-120d can be an image sensor that includes a pixel cell array comprising an plurality of pixel cells (e.g., a two-dimensional (2D) pixel cell array) and configured to generate image data representing different fields of view along different directions toward the user, in particular toward one or more features of a face 135 of the user. For example, the sensors 120a and 120b may be configured to provide image data representing two fields of view toward a direction A along the Z axis, whereas sensor 120c may be configured to provide image data representing a field of view toward a direction B along the X axis, and sensor 120d may be configured to provide image data representing a field of view toward a direction C along the X axis. The sensors 120a and 120b can be used to capture front views of the user's facial features, e.g., the nose, eye, lips, the entire face 135, etc. The sensors 120c and 120d can be used to capture side views of the user's facial features. In some embodiments, the optical sensors 120a-120d are silicon-based. For example, each of the optical sensors 120a-120d can be a complementary metal oxide semiconductor (CMOS) sensor.

The NED 100 can include additional optical sensors (not shown) configured to provide image data representing fields of view away from the user, e.g., directed toward the external environment. Such additional sensors could be used as input devices to control or influence the display content of the NED 100, including to provide an interactive VR/AR/MR experience to the user. For example, in some embodiments, additional sensors could provide images of the external environment to a location tracking system of the NED 100 to track a location and/or a path of movement of the user in the external environment. The NED 100 could then update image data provided to display device 110 based on, for example, the location and orientation of the user, to provide the interactive experience.

The NED 100 may further include one or more active illuminators 130 configured to project light toward the user and/or toward the external environment. Active illuminators are activated using electrical signals that cause the illuminators to project light. The light projected can be associated with different frequency spectrums (e.g., visible light, infrared (IR) light, near infrared (NIR) light, ultra-violet (UV) light, etc.) and can serve various purposes. For example, illuminator 130 may project light and/or light patterns in a dark environment (or in an environment with little or no IR light, NIR light, etc.) to assist sensors 120a-120d in capturing 2D or 3D images of the face 135 of the user. The illumination patterns formed by the illuminator 130 can be placed within a field of view of the user and can be reflected off one or more eyes of the user. In some embodiments, a separate illuminator 130 is used for illuminating the left and right eyes. The illumination patterns produce light that can be reflected off an external surface of the eye (e.g., the cornea) or an internal surface (e.g., the retina). Images of the reflected patterns captured by the sensors 120a-120d can be used to perform biometric authentication as well as eye tracking (e.g., determining an eye gaze of the user).

Another active illuminator (not shown) could be used to project light and/or light patterns for capturing images of objects in the external environment. The images of the objects could be used, for example, to track the head movement or location of the user based on distances to the objects, where the distances are determined by the NED 100 using the captured images. Optical sensors, including the sensors 120a-120d, can be operated in a first mode for 2D sensing and in a second mode for 3D sensing. Captured 2D images can be merged with other captured 2D images or merged with captured 3D images to provide more robust tracking of facial features as well as tracking of the location of the user, the head movement of the user, etc.

Figure 2:
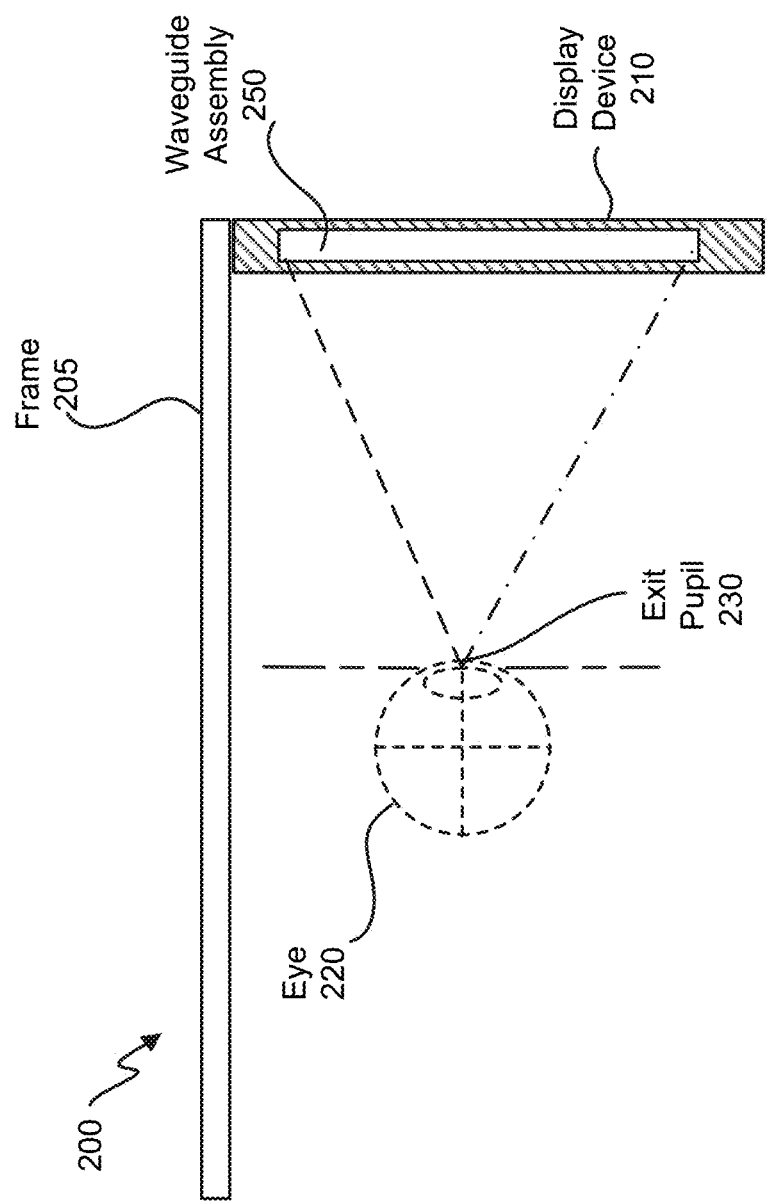
FIG. 2 shows a cross-sectional view of near-eye display, in accordance with an embodiment.

FIG. 2 shows a cross section of an NED 200. The NED 200 may correspond to the NED 100. The NED 200 includes a frame 205 and a display device 210 with at least one waveguide assembly 250. The display device 210 is operable to present image content to the user and includes the waveguide assembly 250, which is configured to direct light from one or more images to an eye 220 of the user. When placed into an operative position with respect to the user, e.g., when the user wears the NED 200, the NED 200 forms an exit pupil 230 at a location where the eye 220 is positioned in an eyebox region. For purposes of illustration, FIG. 2 shows the cross section associated with a single eye 220 and a single waveguide assembly 250, but a second waveguide assembly can be used for a second eye of the user.

The waveguide assembly 250 is configured to direct the image light to the eye 220 through the exit pupil 230. The waveguide assembly 250 may be composed of one or more materials (e.g., plastic, glass, etc.) with one or more refractive indices. In some embodiments, the NED 200 includes one or more optical elements between the waveguide assembly 250 and the eye 220. The waveguide assembly 250 may be composed of one or more materials with one or more refractive indices that effectively minimize the weight and widen a field of view (FOV) of the NED 200.

The NED 200 can include one or more optical elements (not shown) between the waveguide assembly 250 and the eye 220. The optical elements may form an optics system that acts to, e.g., correct aberrations in image light emitted from the waveguide assembly 250, magnify image light emitted from the waveguide assembly 250, some other optical adjustment of image light emitted from the waveguide assembly 250, or some combination thereof. Example optical elements include an aperture, a Fresnel lens, a convex lens, a concave lens, a filter, a reflector, or any other suitable optical element that affects image light.

Figure 3:
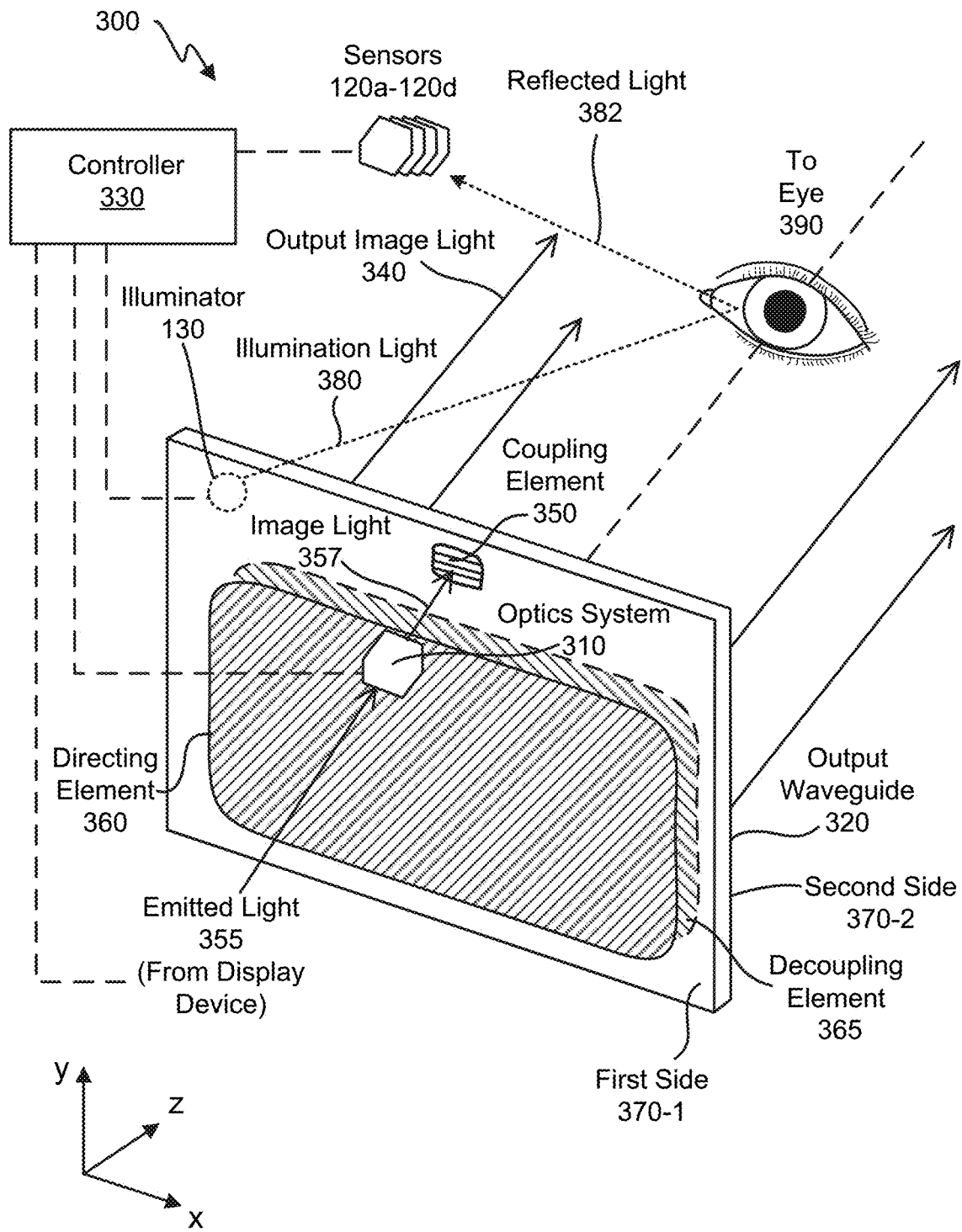
FIG. 3 shows an isometric view of a waveguide assembly, in accordance with an embodiment.

FIG. 3 shows an isometric view of a waveguide assembly 300. In some embodiments, the waveguide assembly 300 is a component of a display device in an NED (e.g., waveguide assembly 250). In other embodiments, the waveguide assembly 300 is a separate component located along an optical path between the display device and an eye 390 of the user. The waveguide assembly 300 includes an optics system 310, an output waveguide 320, a controller 330, a coupling element 350, a directing element 360, and a decoupling element 365.

The waveguide assembly 300 receives emitted light 355 from a display device (not shown) and processes the emitted light 355 through the optics system 310 to generate image light 357. The emitted light 355 is generated by light emitters of the display device. A light emitter can be a light emitting diode (LED), a micro light emitting diode (mLED), a vertical-cavity surface-emitting laser (VCSEL), a photonics integrated circuit (PIC), etc. The light emitters can be organized in a one-dimensional (1D) or 2D array. The emitters can be grouped to form pixels of the display device. For example, an individual pixel may include at least one red emitter, at least one green emitter, and at least one blue emitter.

The optics system 310 comprises one or more optical elements (e.g., one or more lenses, a scanning mirror, etc.) that perform a set of optical processes, including, but not restricted to, focusing, combining, collimating, transforming, conditioning, and scanning processes on the emitted light from the display.

The output waveguide 320 is an optical waveguide that directs the image light 357 to form output image light 340 to the eye 390 of the user. The output waveguide 320 may be composed of one or more materials that facilitate total internal reflection of the image light 357. For example, the output waveguide 320 may be composed of silicon, plastic, glass, and/or polymers. The output waveguide 320 receives the image light 357 at one or more coupling elements 350, and guides the image light 357 to the directing element 360. The coupling element 350 may include, e.g., a diffraction grating, a holographic grating, some other element that couples the image light 357 into the output waveguide 320, or some combination thereof. For example, in embodiments where the coupling element 350 includes a diffraction grating, the pitch of the diffraction grating can be chosen such that total internal reflection occurs and the image light 357 propagates internally toward the decoupling element 365.

The directing element 360 redirects the image light 357 to decoupling element 365 such that the image light 357 is decoupled out of output waveguide 320 via decoupling element 365. Directing element 360 is part of, or affixed to, a first side 370-1 of output waveguide 320. Decoupling element 365 is part of, or affixed to, a second side 370-2 of output waveguide 320, such that directing element 360 is opposed to the decoupling element 365. The second side 370-2 represents a plane along an x-dimension and a y-dimension. Directing element 360 and/or decoupling element 365 may be, e.g., a diffraction grating, a holographic grating, one or more cascaded reflectors, one or more prismatic surface elements, and/or an array of holographic reflectors.

The controller 330 drives the light emitters of the display device to generate the emitted light 355. The controller 330 can also analyze image data captured by the optical sensors 120a-120d. The controller 330 may instruct the display device to form the emitted light 355 based on the analysis of the image data captured by the optical sensors 120a-130d. For example, the emitted light 355 may form interactive image content that is updated in response to the user's eye movements. The controller 330 can also control the optics system 310 to perform the one or more optical processes. For example, the controller 330 may reposition one or more lenses of the optics system 310 to adjust a focus of the image light 357.

In addition to controlling the display device and the optics system 310, the controller 330 can perform biometric authentication of the user based on illumination light 380 generated by the illuminator 130 and corresponding reflected light 382 captured by the optical sensors 120a-120d. In some embodiments, the illuminator 130 and/or the optical sensors 120a-120d may be part of, or affixed to the output waveguide 320, e.g., on the second side 370-2. Alternatively, the illuminator 130 and/or the optical sensors 120a-120d can be located in various positions throughout a head-mounted assembly that incorporates the waveguide assembly 300, e.g., in the positions shown in FIG. 1. Further, although described as being generated by a separate light source (i.e., illuminator 130), in some embodiments illumination light may be generated by one or more light emitting elements of the display device. For example, an illumination pattern can be generated using VCSELs of the display device.

The controller 330 may instruct the illuminator 130 to generate one or more images that contain a light pattern that is reflected off the eye 390 as reflected light 382 toward the sensors 120a-120d. The reflected light 382 can be directly reflected from the eye 390 into the sensors 120a-120d. Alternatively, light reflected off the eye can be further reflected off an optical surface before reaching a sensor. For example, the light may be reflected off an optical surface of the waveguide assembly 300.

As mentioned earlier in the discussion of FIG. 1, optical sensors can be operated to perform 2D or 3D sensing. For 2D sensing, the optical sensors 120a-120d can be operated to generate pixel data representing an intensity of the reflected light 382. For 3D sensing, the optical sensors 320a-320d can be operated to generate pixel data representing a time-of-flight measurement (e.g., a difference between a time at which the illumination light 380 is output by the illuminator 120 and a time at which the reflected light 382 is received by the optical sensors 120a-120d). The optical sensors 120a-120d can be operated to perform 2D and 3D sensing at different times, and to provide the 2D and 3D image data to the controller 330 or to a remote console (not shown) that is part of, or communicatively coupled to, a head-mounted assembly. The controller 330 or remote console can form a 2D or 3D model of one or more facial features using information derived from the 2D and 3D image data. The model may include, for example, a model of the surface of the cornea of the eye 390.

Figure 4:
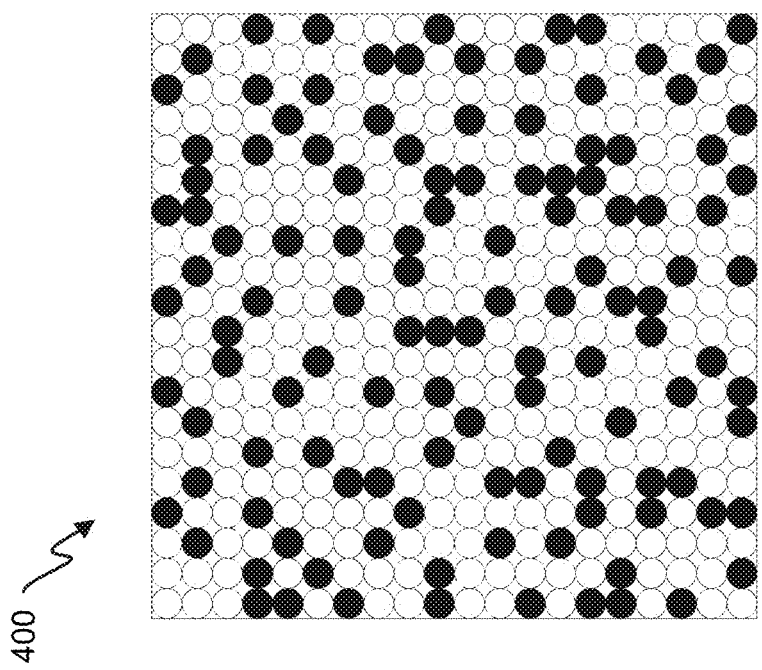
FIG. 4 shows a simplified representation of a reference pattern which may be used to implement one or more embodiments.

FIG. 4 shows a simplified representation of a reference pattern 400 which may be used to implement one or more embodiments. The reference pattern 400 comprises a dense array of geometric features. In the embodiment of FIG. 4, the geometric features are formed by dots that are encoded such that the dots can be individually identified in a reflected pattern. A geometric feature may correspond to a single dot or a group of dots. Each dot represents a point of illumination and may be uniquely encoded. The number of points of illumination may vary and is preferably at least one hundred. In one embodiment, the number of points of illumination is at least one thousand. For simplicity, the dots are shown in black and white, where black indicates illumination points that are turned off and white indicates illumination points that are turned on. However, grey-scale and color patterns are also possible.

Various encoding schemes may be used for encoding the reference pattern 400. For example, the reference pattern 400 may be binary encoded, where a value of 1 corresponds to a state of "on" and a value of 0 corresponds to "off," i.e., a binary data indicating whether a geometric feature is present or absent at a particular position in the reference pattern. Alternatively, the reference pattern may be encoded based on brightness value, e.g., based on a gray-scale value indicating a brightness of a particular geometric feature. In some embodiments, the reference pattern may be a time varying pattern that is temporally encoded or wavelength encoded. For example, a first pattern of dots that output light of a first wavelength and a second pattern of dots that output light of second wavelength may be projected onto the user's eye in alternating frames or in a sequence of frames, in which case wavelength data may indicate which wavelength a particular geometric feature has. Similarly, temporal data may be used to indicate changes in the geometric features over time. Thus, the reference pattern does not have to be a static pattern.

As shown in FIG. 4, the reference pattern 400 is rectilinear, with the dots being arranged along a 2D grid of parallel lines. To facilitate identification, the dots may be regularly spaced apart and non-overlapping. The reference pattern 400 may be generated randomly or pseudo-randomly to meet certain criteria. For example, the dots may be constrained by the rule that in any 3×3 neighborhood or block of dots, there is at least one bright dot and at least one dark dot, such that no 3×3 block is completely bright or completely dark. To facilitate identification of the dots in a reflected pattern, the reference pattern may be generated to have a desired autocorrelation. In one embodiment, the desired autocorrelation is a "spikey" autocorrelation function, in which most of the values produced by convolving the reference pattern with a delayed version of the reference pattern (e.g., the reflected pattern) are relatively small such that the peak values of the convolution (corresponding to locations where the delayed pattern matches the original reference pattern) can be used to easily determine how much the delayed version has been shifted relative to the original reference pattern.

In other words, when the reflected pattern is received, it is not necessarily aligned with the reference pattern. There may be an unknown shift in both the x and y directions between the two patterns. If the reference pattern has a desired (e.g., "spikey") autocorrelation function, it can be easily determined whether alignment has been reached— i.e., when the dot product of the reflected pattern and the reference pattern results in a peak value. In fact, the autocorrelation function of the reference pattern can be chosen to have predictable values at non-zero x and y offsets (e.g. increasing values toward the peak), such that even when the x and y shifts are non-zero, dot products of the reflected pattern and the reference pattern can reveal the value of the relative x and y shifts between the two patterns. Thus, choosing a desired autocorrelation function can greatly facilitate the process of mapping the reflected pattern to the reference pattern.

In some embodiments, the reference pattern 400 may include non-random elements such as fiducial markers. For example, at least some of the dots may correspond to a 2D barcode or a reference image. The use of fiducials may facilitate identification of dots in the reflected pattern. Additionally, dots do not have to be circular or even round, but may instead have other shapes such as square or rectangular.

Figure 5:
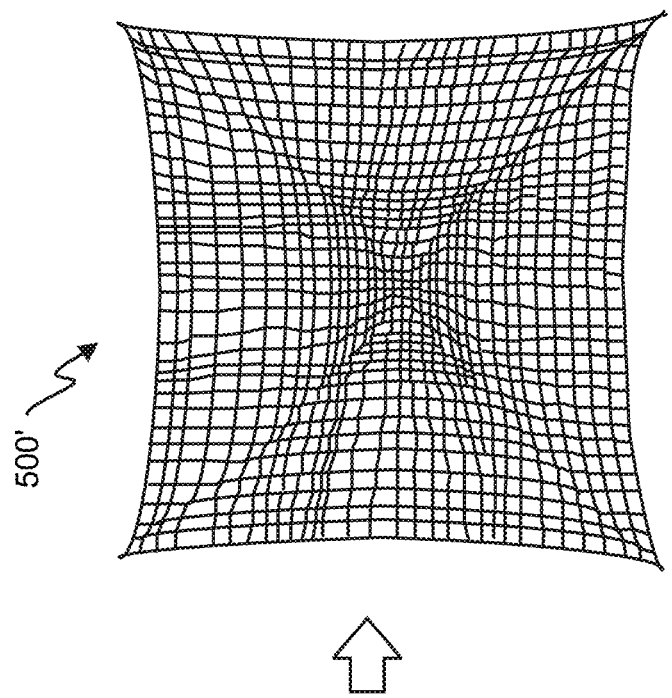
FIG. 5 shows a process for generating an illumination pattern by warping a reference pattern, in accordance with an embodiment.
Figure 5:
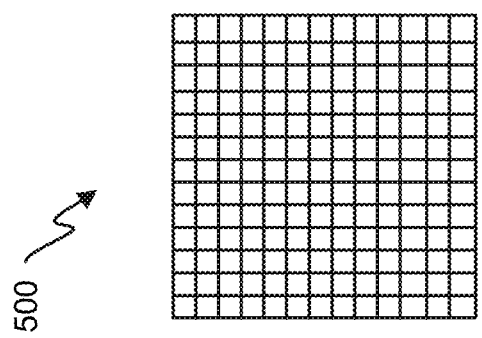

Because the surface of the eye is not flat, projecting a rectilinear pattern such as the reference pattern 400 onto the eye would result in a reflected pattern that is distorted, making identification of dots difficult. To overcome this problem, the illumination pattern may be formed by "pre-warping" (i.e., intentionally distorting) the reference pattern so that the reflected pattern becomes a rectilinear pattern of approximately the same shape as the original, rectilinear reference pattern, e.g., rectilinear (if the shape of the user's eye matches exactly the shape of the eye model used to generate the illumination pattern) or substantially rectilinear (if the shape of the user's eye deviates from the eye model used to generate the illumination pattern). Thus, the reflected pattern may also include a set of dots arranged along a 2D grid, with a majority of the dots being located along straight lines in the x and y directions. FIG. 5 illustrates this pre-warping concept. In FIG. 5, a reference pattern 500 has been warped to form an illumination pattern 500'. For simplicity, the pattern of bright and dark dots is omitted in FIG. 5. The pre-warping of the reference pattern may be performed based on a model of a typical or ideal human eye, e.g., assuming an average corneal radius located at an average position of a user's eye as seen by an optical sensor when the HMD is worn, with the assumption that the eye is completely spherical.

Figure 6:
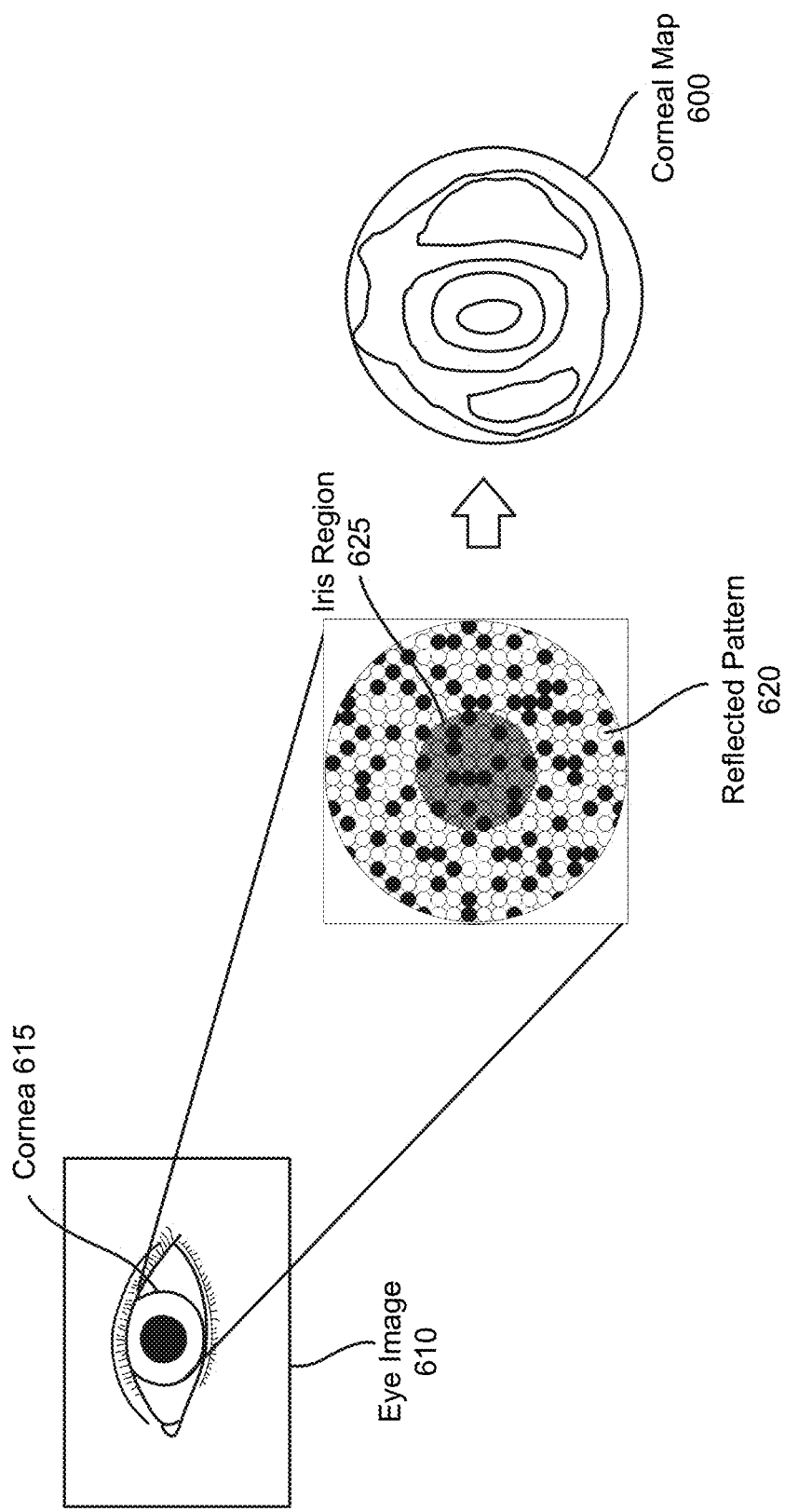
FIG. 6 shows a process for generating a corneal map, in accordance with an embodiment.

FIG. 6 shows a process for generating a corneal map 600 according to an embodiment. The process begins with capturing an eye image 610 that includes at reflected pattern corresponding to at least a portion of an illumination pattern. The illumination pattern is projected onto a surface of the user's eye, including onto a cornea 615. The eye image 610 may be captured using an optical sensor, e.g., the sensors 120a-120d discussed in connection with FIGS. 1 and 3. The eye image 610 may include other features of the user's face that are not needed for corneal topography. These extraneous features may be removed by applying image processing to the eye image 610, e.g., cropping the eye image 610 to remove portions of the eye image that are outside of the area of the cornea.

The corneal portion of the eye image 610 includes a reflected pattern 620, which corresponds to at least a portion of an illumination pattern that is reflected off the exterior surface of the cornea 615. The reflected pattern 620 includes a pattern of dots, with a darker area corresponding to an iris region 625. In some embodiments, the projected illumination pattern is larger than the area of the cornea so that the reflected pattern includes only part of the illumination pattern. In other embodiments, the projected illumination pattern may be smaller than the area of the cornea so that the entire illumination pattern is represented in the reflected pattern. The reflected pattern 620 can be compared to a reference pattern to determine the shape of the cornea and form the corneal map 600. Differences between the reference pattern and the reflected pattern may indicate deviations of the user's cornea from a modeled or ideal corneal shape.

Example methods will now be described. The methods can be performed using a system according to an embodiment, e.g., using an HMD with an illuminator capable of projecting an illumination pattern onto a surface of the user's eye, and one or more processors or control units operable to perform the various processing steps.

Figure 7:
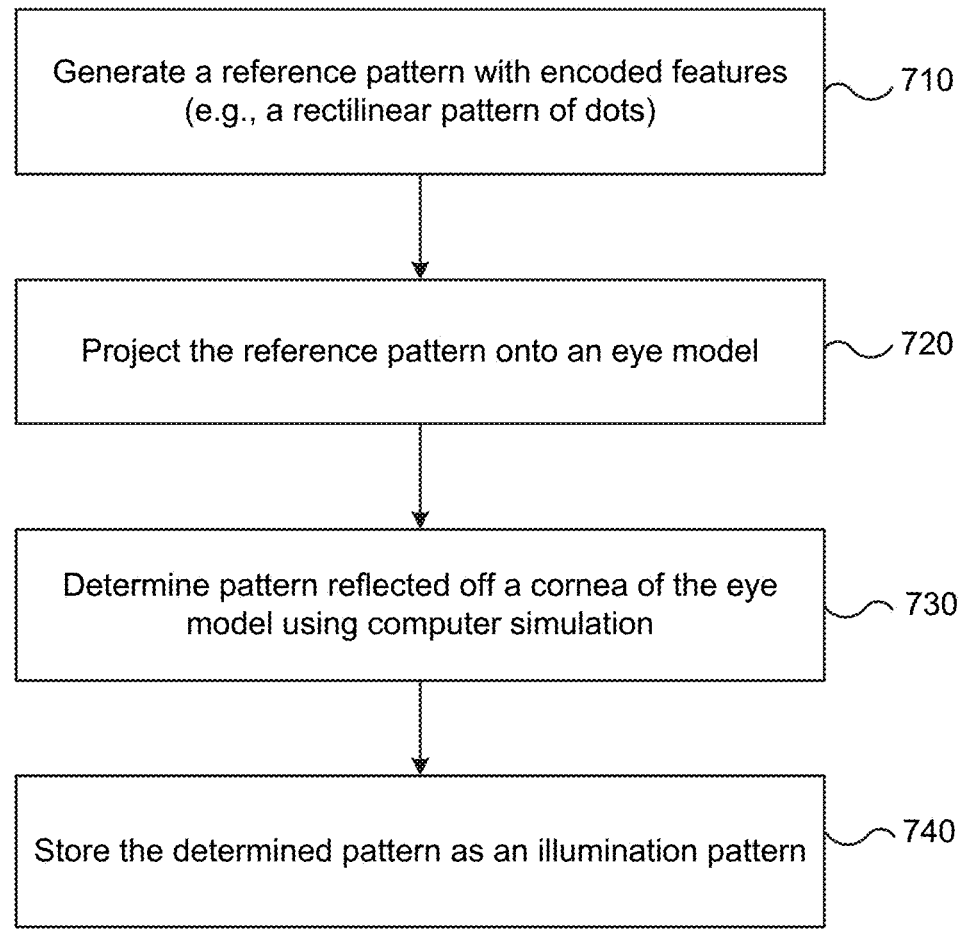
FIG. 7 is a flowchart of a method for generating an illumination pattern, in accordance with an embodiment.

FIG. 7 is a flowchart of a method 700 for generating an illumination pattern, according to an embodiment. The method 700 transforms a reference pattern to produce a warped version of a reference pattern for use as an illumination pattern. At step 710, a reference pattern is generated to include encoded features such as a rectilinear pattern of dots.

At step 720, the reference pattern is projected onto an eye model, which may correspond to a typical or ideal human eye.

At step 730, a pattern reflected off a cornea of the eye model is determined using computer simulation, which may include, for example, ray tracing to locate the corresponding positions of dots in the reflected pattern.

At step 740, the pattern determined in step 730 is stored as an illumination pattern in a computer-readable memory that can subsequently be accessed for projecting the illumination pattern onto a user's eye. The illumination pattern includes geometric features corresponding to those of the reference pattern, and thus the same number of points of illumination, but shaped differently. The illumination pattern may be encoded for storage using the same encoding scheme as the reference pattern.

Figure 8:
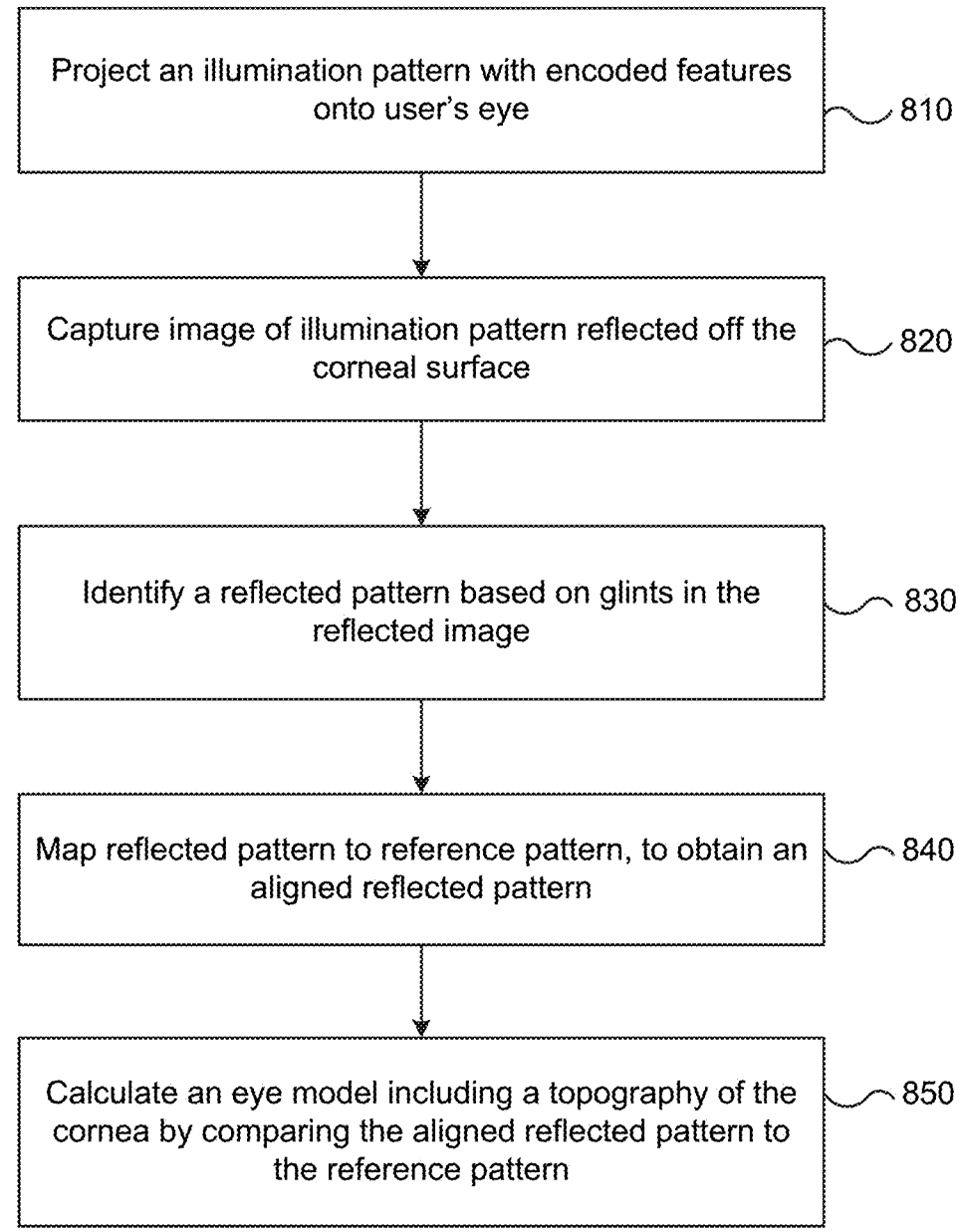
FIG. 8 is a flowchart of a method for performing corneal topography, according to an embodiment.

FIG. 8 is a flowchart of a method 800 for performing corneal topography, according to an embodiment. At step 810, an illumination pattern including encoded features is projected onto a user's eye. The illumination pattern is based on a reference pattern (e.g., a warped version of a rectilinear reference pattern) and corresponds to selective illumination of dots arranged along a two-dimensional grid.

At step 820, an image of the illumination pattern as reflected off the surface of the user's cornea is captured using one or more optical sensors.

At step 830, a reflected pattern is identified by based on glints in the reflected image. The identification can be based on characteristics of the glints such as size, position relative to neighboring glints (e.g., distance or orientation), intensity, etc. Various identification techniques may be applied depending on how the illumination pattern was encoded.

At step 840, the reflected pattern is mapped to a reference pattern to obtain an aligned reflected pattern. The mapping may include determining an orientation of the reflected pattern relative to the reference pattern, determining correspondences between dots in the reflected pattern and dots in the reference pattern, and determine how much the reflected pattern has been shifted (e.g., in an x direction and/or a y direction) relative to the reference pattern.

Steps 820 to 840 may be repeated to capture, identify, and align reflected patterns in multiple images corresponding to the user's eye in different positions. For example, the user may be instructed to look in one or more directions (e.g., left and right) to capture reflections over the entire corneal surface. Information from one or more captured images can then be applied to produce a model of the user's eye in step 850.

At step 850, the model of the user's eye, which includes a topography of the cornea, is calculated using the information from the captured image(s), e.g., by comparing an aligned reflected pattern to a reference pattern that corresponds to the illumination pattern used in step 810. The calculation may include solving for the 3D shape of the cornea to determine the topography of the cornea.

Figure 9:
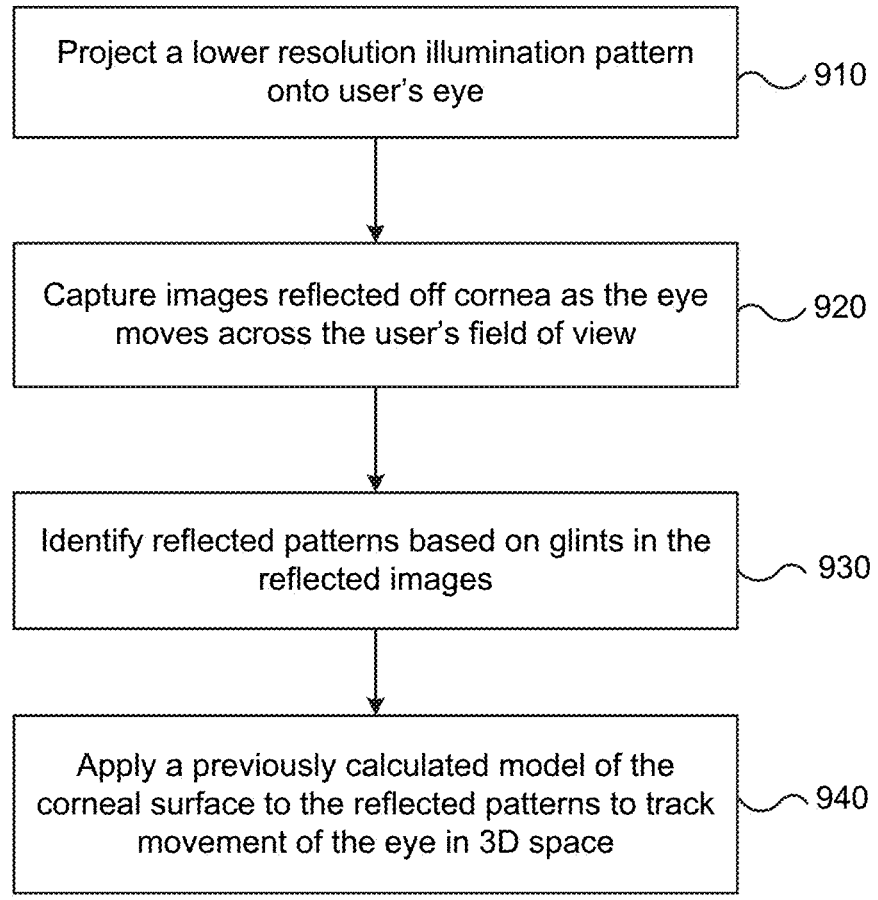
FIG. 9 is a flowchart of a method for eye tracking based on a model of the surface of a user's cornea, in accordance with an embodiment.

FIG. 9 is a flowchart of a method 900 for eye tracking based on a model of the surface of the user's cornea, according to an embodiment. For purposes of eye tracking, the cornea does not need to be continuously remapped (e.g., on a frame-by-frame basis). Instead, once a model of the surface of the cornea has been calculated (e.g., during a calibration phase in which the method 800 is performed) the model can be fitted to new observations about the position of the cornea. The method 900 can be performed using the same illumination pattern as that which was previously used to generate a model of the user's eye. Alternatively, a less resource intensive illumination pattern may be used. Thus, at step 910, a lower resolution illumination pattern is projected onto the user's eye. The lower resolution illumination pattern may, for example, correspond to the earlier illumination pattern with one or more illumination points deactivated in order to conserve power. Thus, the lower resolution illumination pattern may comprise a subset of the geometric features of the earlier illumination pattern. In some embodiments, the lower resolution illumination pattern may include the same illumination points, but with lower intensities that are still sufficient for producing glints.

At step 920, images of the lower resolution illumination pattern are captured by one or more optical sensors as the eye moves across the user's field of view.

At step 930, reflected patterns are identified based on glints in the reflected images.

At step 940, a previously calculated model of the corneal surface of the user's eye is applied to the reflected patterns to track the movement of the eye in 3D space (e.g., with six degrees of freedom) by estimating the shape and pose of the eye using techniques such as non-linear least squares analysis. Thus, the previously calculated model of the corneal surface is used as a reference against which the reflected patterns are analyzed to determine a correspondence between movement of the eye and changes in the reflected patterns. For example, the analysis may determine how much the eye has shifted relative to the position of the eye when the model of the corneal surface was generated. In some embodiments, glint information may be combined with information obtained from the images about the position of one or more eye features such as the pupil or iris. For example, a shift in the corneal surface applied to a plane of the pupil to calculate a location in 3D space for a center of the pupil. Thus, eye tracking may be performed using glints only or glints in combination with an eye feature.

Figure 10:
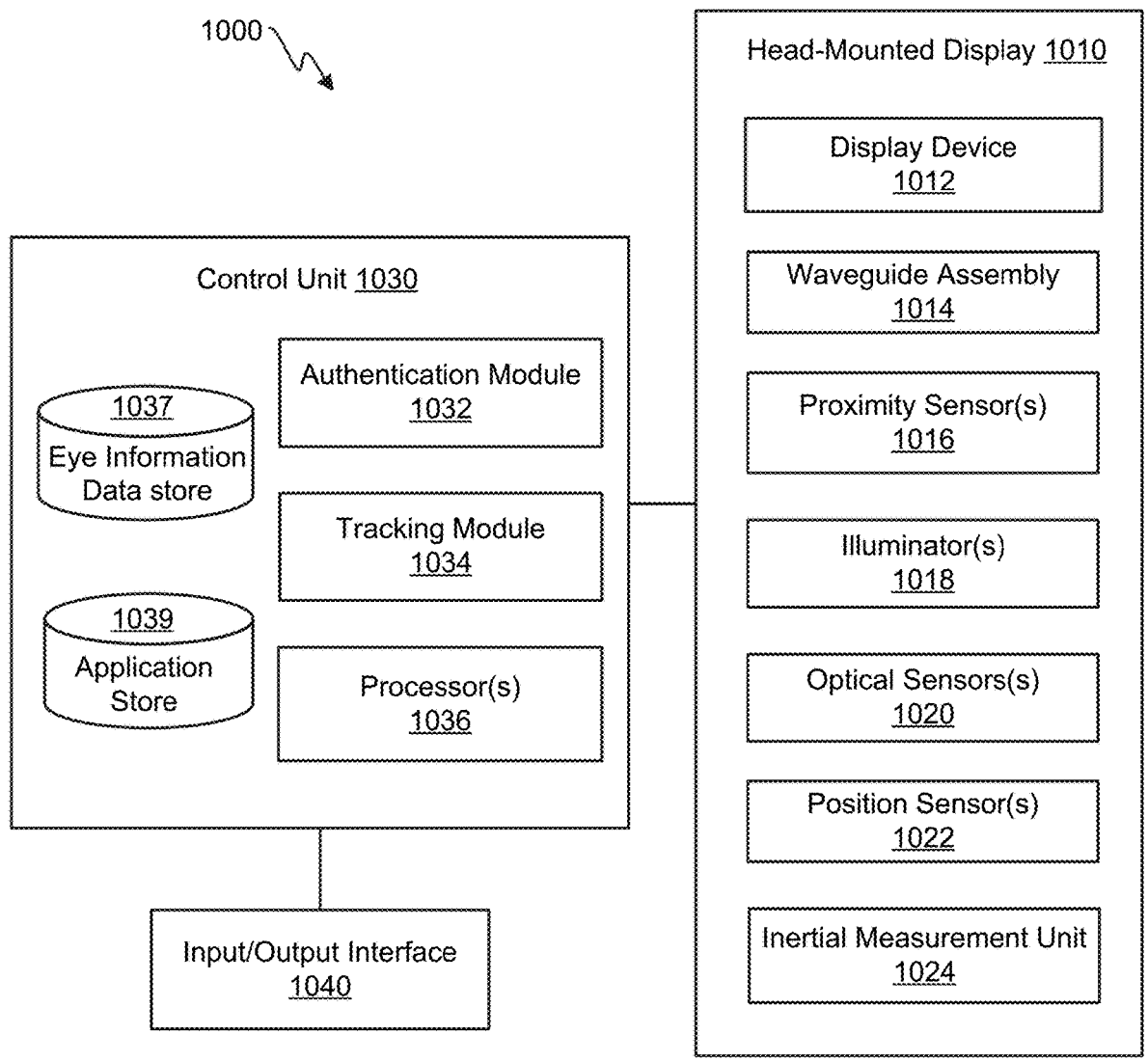
FIG. 10 is a block diagram of a system in which one or more embodiments may be implemented.

FIG. 10 is a block diagram of a system 1000 in which one or more embodiments may be implemented. The system 1000 includes an HMD 1010, a control unit 1030, and an input/output (I/O) interface 1040. The HMD 1010 includes a display device 1012, a waveguide assembly 1014, at least one proximity sensor 1016, at least one illuminator 1018, at least one optical sensor 1020, at least one position sensor 1022, and an inertial measurement unit 1024.

The display device 1012 includes a display screen for presenting visual media, such as images and/or video, to a user. The display device 1012 may correspond to one of the earlier described display devices, e.g., the display device 110 or the display device 210. In addition to visual media, the HMD 1010 may include an audio output device (not shown) for presenting audio media to the user, e.g., in conjunction with the presentation of the visual media.

The waveguide assembly 1014 is part of, or affixed to, the display device 1012 and may correspond to the waveguide assembly 250 in FIG. 2 or the waveguide assembly 300 in FIG. 3. The waveguide assembly 1014 may also include an optical substrate for directing a reflected illumination pattern toward the optical sensor(s) 1020.

The proximity sensor 1016 can be any sensor capable of detecting that the user is wearing the HMD 1010. For example, the proximity sensor 1016 can be a simple mechanical switch that is activated when the user's head is pressed against a frame of the HMD 1010. The proximity sensor 1016 can be a resistive or capacitive touch sensor configured to detect contact with the user's head based on electrical measurements. In some embodiments, the proximity sensor 1016 is an optical sensor. For purposes of detecting whether the user is wearing the HMD 1010, the proximity sensor 1016 does not have to be an imaging sensor. For example, the proximity sensor 1016 can be a passive IR sensor that detects the user's presence based on a change in the intensity of infrared light emitted from nearby objects. Alternatively, the proximity sensor 1016 can be an active IR sensor that emits infrared light and detects the resulting infrared reflections. The proximity sensor 1016 can be used to verify the user's presence before initiating corneal topography, eye tracking, and/or biometric authentication.

The illuminator 1018 is an electrically triggered light source that generates light for use in connection with corneal topography, eye tracking, and/or biometric authentication. The illuminator 1018 may correspond to the illuminator 130. The illuminator 1018 can be placed in a frame of the HMD 1010 or integrated into an optical component such as the display device 1012 or the waveguide assembly 1014.

The optical sensor 1020 is an image sensor configured to capture 2D and/or 3D image data, for example, a 2D image of the user's eye. The optical sensor 1020 may correspond to one of the optical sensors 120a-120d.

The inertial measurement unit 1024 is an electronic device that generates data indicating an estimated position of the HMD 1010 relative to an initial position of HMD 1010, based on measurement signals received from the position sensor 1022. The measurement signals can include, for example, signals indicative of roll, pitch, yaw, or acceleration.

The I/O interface 1040 is a device that allows the user to send action requests to the control unit 1030. An action request is a request to perform a particular action. For example, an action request may be to start or end an application or to perform a particular action within the application.

The control unit 1030 is configured to direct the operation of the HMD 1010 and can implement any of the controller functions described earlier including, for example, selecting content for presentation on the display device 1012 and activating the illuminator 1018 to project an illumination pattern. The control unit 1030 includes an authentication module 1032, a tracking module 1034, one or more processors 1036, an eye information data store 1037, and an application store 1039. The control unit 1030 can include components that are integrated into the HMD 1010. In some embodiments, one or more components of the control unit 1030 are remotely located. For example, the eye information data store 1037 can be located on a remote server or distributed between a memory of the control unit 1030 and a remote server.

The eye information data store 1037 stores eye information for a user of the HMD 1010. The eye information may include a 3D eye model that includes a topography of a cornea of the user, e.g., a model of the corneal surface generated using one or more of the techniques described earlier. The eye model stored in the eye information data store 1037 can be compared to an eye model generated using the HMD 1010 to authenticate the user or perform eye tracking. The eye information data store 1037 may also store one or more reference patterns and one or more corresponding illumination patterns.

The application store 1039 stores one or more applications for execution by the control unit 1030. An application is a set of instructions executable by a processor, for example instructions that cause the processor to generate content for presentation to the user on the display device 1012. Examples of applications include: gaming applications, conferencing applications, video playback application, or other suitable applications.

The authentication module 1032 can be implemented in hardware and/or software and is configured to perform a biometric authentication of the user through activation of the illuminator 1018 and analysis of the resulting image data captured by the optical sensor 1020. Execution of an application or access to certain functions of an application in the application store 1039 can be conditioned upon successful authentication of the user.

The tracking module 1034 can be implemented in hardware and/or software and is configured to track changes in the position of the HMD 1010 and/or the position of the user's facial features. For example, the tracking module 1034 may track the movements of the HMD 1010 and correlate the HMD movements to movement of the user's head. The tracking module 1034 may also track the user's eye movements using a stored eye model.

The processor 1036 executes instructions from applications stored in the application store 1039 and/or instructions provided to the processor 1036 by the authentication module 1032 or the tracking module 1034. The processor 1036 can receive various items of information used in the applications. This includes, for example, position information, acceleration information, velocity information, captured images, and/or reflected patterns. Information received by processor 1036 may be processed to produce instructions that determine content presented to the user on the display device 1012.

The foregoing description of the embodiments of the disclosure has been presented for the purpose of illustration; it is not intended to be exhaustive or to limit the disclosure to the precise forms disclosed. Persons skilled in the relevant art can appreciate that many modifications and variations are possible in light of the above disclosure.

Some portions of this description describe the embodiments of the disclosure in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, and/or hardware.

Steps, operations, or processes described may be performed or implemented with one or more hardware or software modules, alone or in combination with other devices. Although the steps, operations, or processes are described in sequence, it will be understood that in some embodiments the sequence order may differ from that which has been described, for example with certain steps, operations, or processes being omitted or performed in parallel or concurrently. In some embodiments, a software module is implemented with a computer program product comprising a computer-readable medium containing computer program code, which can be executed by a computer processor for performing any or all of the steps, operations, or processes described.

Embodiments of the disclosure may also relate to an apparatus for performing the operations described. The apparatus may be specially constructed for the required purposes, and/or it may comprise a general-purpose computing device selectively activated or reconfigured by a computer program stored in the computer. Such a computer program may be stored in a non-transitory, tangible computer readable storage medium, or any type of media suitable for storing electronic instructions, which may be coupled to a computer system bus. Furthermore, any computing systems referred to in the specification may include a single processor or may be architectures employing multiple processor designs for increased computing capability.

The language used in the specification has been principally selected for readability and instructional purposes, and it may not have been selected to delineate or circumscribe the inventive subject matter. It is therefore intended that the scope of the disclosure be limited not by this detailed description, but rather by any claims that issue on an application based hereon. Accordingly, the disclosure of the embodiments is intended to be illustrative, but not limiting, of the scope of the disclosure, which is set forth in the following claims.

What is claimed is:

1. A method, comprising:
    determining, by one or more processors of a control unit for a head-mounted assembly, an illumination pattern to be projected over a sequence of frames onto an eye of a user wearing the head-mounted assembly, wherein:
        the sequence of frames includes a first frame and a second frame;
        the first frame includes a first pattern of dots;
        the second frame includes a second pattern of dots;
        the first pattern and the second pattern are non-rectilinear patterns configured to become substantially rectilinear approximations of one or more corresponding reference patterns when reflected off an eye-shaped surface, wherein each reference pattern comprises dots arranged according to a two-dimensional grid having straight lines that define rows and columns in which the dots are arranged, and wherein each non-rectilinear pattern represents a transformation of a corresponding reference pattern to distort the lines of the two-dimensional grid; and
        the first pattern differs from the second pattern with respect to a wavelength of light used to project one or more dots, a position of one or more dots, or both;
    after determining the illumination pattern, causing, by the control unit, one or more illuminators in the head-mounted assembly to project the illumination pattern over the sequence of frames and onto the eye of the user; and
    calculating, by the one or more processors, an eye model based on reflections of the illumination pattern as projected over the sequence of frames and onto the eye of the user, wherein the eye model characterizes a topography of a cornea of the eye of the user.

2. The method of claim 1, wherein the first pattern is projected using a different wavelength of light than the second pattern.

3. The method of claim 1, wherein the illumination pattern is projected using an illuminator that operates as a single point source of light.

4. The method of claim 3, wherein the illumination pattern is holographically projected.

5. The method of claim 1, further comprising:
    aligning, by the one or more processors, a reflected pattern to a reference pattern, the aligning comprising determining, based on a dot product of the reflected pattern and the reference pattern, an amount by which the reflected pattern is shifted relative to the reference pattern, wherein the eye model is calculated using the reflected pattern after the reflected pattern has been aligned.

6. The method of claim 5, wherein the illumination pattern is configured such that the dot product increases as the reflected pattern becomes less shifted relative to the reference pattern.

7. The method of claim 1, wherein some of the dots in the illumination pattern are random or pseudorandom, and wherein the illumination pattern further includes dots that form a fiducial marker.

8. The method of claim 7, wherein the fiducial marker is a two-dimensional barcode.

9. The method of claim 1, wherein illumination pattern comprises non-circular dots.

10. The method of claim 1, further comprising:
    switching to a lower resolution illumination pattern after calculating the eye model, wherein the lower resolution illumination pattern comprises a subset of dots in the illumination pattern or the same dots in the illumination pattern but with lower intensity; and
    tracking eye movement of the user based on reflections of the lower resolution illumination pattern.

11. A control unit for a head-mounted assembly, the control unit comprising one or more processors configured to:
    determine an illumination pattern to be projected over a sequence of frames onto an eye of a user wearing the head-mounted assembly, wherein:
        the sequence of frames includes a first frame and a second frame;
        the first frame includes a first pattern of dots;
        the second frame includes a second pattern of dots;
        the first pattern and the second pattern are non-rectilinear patterns configured to become substantially rectilinear approximations of one or more corresponding reference patterns when reflected off an eye-shaped surface, wherein each reference pattern comprises dots arranged according to a two-dimensional grid having straight lines that define rows and columns in which the dots are arranged, and wherein each non-rectilinear pattern represents a transformation of a corresponding reference pattern to distort the lines of the two-dimensional grid; and
        the first pattern differs from the second pattern with respect to a wavelength of light used to project one or more dots, a position of one or more dots, or both;
    after determining the illumination pattern, cause one or more illuminators in the head-mounted assembly to project the illumination pattern over the sequence of frames and onto the eye of the user; and calculate an eye model based on reflections of the illumination pattern as projected over the sequence of frames and onto the eye of the user, wherein the eye model characterizes a topography of a cornea of the eye of the user.

12. The control unit of claim 11, wherein the control unit is configured to cause the first pattern to be projected using a different wavelength of light than the second pattern.

13. The control unit of claim 11, wherein the control unit is configured to cause the illumination pattern to be projected using an illuminator that operates as a single point source of light.

14. The control unit of claim 13, wherein the illuminator is configured to holographically project the illumination pattern.

15. The control unit of claim 11, wherein:
the control unit is configured to align a reflected pattern to a reference pattern;
to align the reflected pattern, the one or more processors of the control unit are configured to determine, based on a dot product of the reflected pattern and the reference pattern, an amount by which the reflected pattern is shifted relative to the reference pattern; and
the one or more processors are configured to calculate the eye model using the reflected pattern after the reflected pattern has been aligned.

16. The control unit of claim 15, wherein the illumination pattern is configured such that the dot product increases as the reflected pattern becomes less shifted relative to the reference pattern.

17. The control unit of claim 11, wherein some of the dots in the illumination pattern are random or pseudorandom, and wherein the illumination pattern further includes dots that form a fiducial marker.

18. The control unit of claim 17, wherein the fiducial marker is a two-dimensional barcode.

19. The control unit of claim 11, wherein illumination pattern comprises non-circular dots.

20. The control unit of claim 11, wherein the control unit is further configured to:
switch to a lower resolution illumination pattern after calculating the eye model, wherein the lower resolution illumination pattern comprises a subset of dots in the illumination pattern or the same dots in the illumination pattern but with lower intensity; and
track eye movement of the user based on reflections of the lower resolution illumination pattern.

* * * * *